(12) United States Patent
Ma et al.

(10) Patent No.: US 7,065,920 B2
(45) Date of Patent: Jun. 27, 2006

(54) CONTAMINANT REMOVAL BY ADDITIONAL FERNS

(75) Inventors: Lena Q. Ma, Gainesville, FL (US); Thomas Luongo, High Springs, FL (US); Mrittunjai Srivastava, Gainesville, FL (US); Nandita Singh, Kaiserbagh (IN)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/961,932

(22) Filed: Oct. 8, 2004

(65) Prior Publication Data

US 2005/0082221 A1   Apr. 21, 2005

Related U.S. Application Data

(60) Continuation-in-part of application No. 10/825,993, filed on Apr. 16, 2004, which is a continuation-in-part of application No. 10/756,237, filed on Jan. 12, 2004, which is a continuation-in-part of application No. 09/948,969, filed on Sep. 7, 2001, now abandoned, which is a division of application No. 09/546,941, filed on Apr. 11, 2000, now Pat. No. 6,302,942, which is a continuation-in-part of application No. 09/471,566, filed on Dec. 23, 1999, now Pat. No. 6,280,500.

(60) Provisional application No. 60/129,203, filed on Apr. 14, 1999.

(51) Int. Cl.
C22B 3/18 (2006.01)
C22B 3/24 (2006.01)

(52) U.S. Cl. ............ 47/58.1; 800/298; 210/602; 210/682; 75/710; 75/711; 75/712

(58) Field of Classification Search .......... 75/711, 75/712, 710; 800/298, 295; 210/602, 682; 47/58.1
See application file for complete search history.

(56) References Cited

U.S. PATENT DOCUMENTS

| | | | | |
|---|---|---|---|---|
| 5,000,852 A | * | 3/1991 | Tel-Or et al. | 210/602 |
| 5,364,451 A | | 11/1994 | Raskin | 75/710 |
| 5,785,735 A | * | 7/1998 | Raskin et al. | 75/711 |
| 5,809,693 A | * | 9/1998 | Chet et al. | 47/58 |
| 5,917,117 A | | 6/1999 | Ensley | 75/722 |
| 5,927,005 A | | 7/1999 | Gardea-Torresdey | 47/58.1 |
| 5,944,872 A | | 8/1999 | Chaney | 75/712 |
| 6,005,092 A | | 12/1999 | Shoseyov | 536/23.6 |
| 6,280,500 B1 | * | 8/2001 | Ma et al. | 75/711 |
| 6,302,942 B1 | * | 10/2001 | Ma et al. | 75/712 |

OTHER PUBLICATIONS

Ho et al. Bull. Environ. Contam. Toxicol. vol. 35, pp. 430-438, 1985.*

Noctor et al. Journal of Experimental Botany, vol. 49, No. 321, pp. 623-647, Apr. 1998.*

Bennett, F.A., E.K. Tyler, R.R. Brooks, P.E.H. Gregg, and R.B. Stewart (1998). Fertilisation of Hyperaccumulators to Enhance their Potential for Phytoremediation and Phytomining. *Plants that Hyperaccumulate Heavy Metals*. R. R. Brooks. New York, CAB International: 249-259.

Cullen, W.R. and K.J. Reimer (1989). "Arsenic Speciation in the Environment." *Chem. Rev.*(89): 713-764.

Cunningham, S.D., J.R. Shann. D.E. Crowley, and T.A. Anderson (1997). Phytoremediation of Contaminated Water and Soil. *Phytoremediation of Soil and Water Contaminants*. E.L. Kruger, T.A. Anderson and J.R. Coats. Washington, DC, American Chemical Society: 2-15.

Dix, M.E.,N.B. Klopfenstein, J.W. Zhang, S.W. Workman, and M.S. Kim (1997). Potential Use of Populus for Phytoremediation of Environmental Pollution in Riparian Zones.

Ebbs, S.D., M.M. Lasat, D.J. Brady, J. Comish. R. Gordon. and L.V. Kochian (1997). "Phytoextraction of Cadmium and Zinc from a Contaminated Soil." *Journal of Environmental Quality* 26: 1424-1430.

(Continued)

Primary Examiner—Medina A. Ibrahim
(74) *Attorney, Agent, or Firm*—Brian S. Steinberger; Law Offices of Brian S. Steinberger, P.A.

(57) ABSTRACT

Processes, methods, materials and compositions for phytoremediating contaminated waters, which have been contaminated with pollutants such as arsenic. Fern plants that include *Pteris* and non-*Pteris* fern plants can be used to accumulate pollutants from contaminated water, including aqueous solution, waste water, ground water, surface water, combinations thereof. Pollutants and contaminants can be removed from the water, soil and wetland type environment via phytoremediation through roots and fronds as well as by applying excised portions of plants such as leaflets (cut-off fronds). The biomass can be harvested and readily disposed of, or can be treated to recover the pollutants and contaminants.

54 Claims, 4 Drawing Sheets

OTHER PUBLICATIONS

Fowler, B.A. (1977). Toxicology of Environmental Arsenic. *Toxicology of Trace Elements*. R.A. Goyer and M.A. Mehlman. New York, NY, Hemisphere Publishing Corporation. 2: 79-122.

Grant, C. and A.J. Dobbs (1977). "The Growth and Metal Content of Plants Grown in Soil Contaminated by a Copper/Chrome/Arsenic Wood Preservative." *Environ. Pollut.* 14: 213-226.

Huang, J.W., M.J. Blaylock. Y. Kapulnik, and B.D. Ensley (1998). "Phytoremediation of Uranium-Contaminated Soils: Role of Organic Acids in Triggering Uranium Hyperaccumulation in Plants." *Environ. Sci. Technol.* 32: 2004-2008.

Kramer, U., R.D. Smith, W.W. Wenzel, I. Raskin, and D.E. Salt(1997). "The Role of Metal Transport and Tolerance in Nickel Hyperaccumulation by Thlaspi goesingense Halacsy." *Plant Physiol.*(115): 1641-1650.

Lasat, M. M., M. Fuhrmann. S. D. Ebbs, J. E. Cornish, and L. V. Kochian (1998). "Phytoremediation of a Radiocesium-Contaminated Soil: Evaluation of Cesium-137 Bioaccumulation in the Shoots of Three Plant Species." *Journal of Environmenatal Quality* 27: 165-169.

Ma, L.Q., F. Tan, and W.H. Harris. 1997. Concentration and distribution of 11 elements in Florida soils. J. Environ. Qual. 26: 769-775.

McGrath, S.P. (1998). Phytoextraction for Soil Remediation. *Plants that Hyperaccumulate Heavy Metals*. R.R. Brooks. New York, NY, CAB International: 261-287.

Porter, E.K. and P.J. Peterson (1977). Arsenic Tolerance in Grasses Growing on Mine Waste. *Environ. Pollut.* 14: 255-265.

Squibb, K.S. and B.A. Fowler (1983). The Toxicity of Arsenic and its Compounds. *Biological and Environmental Effects of Arsenic*. B.A. Fowler. Research Triangle Park, NC, Elsevier Science Publishers: 233-269.

Walsh, L.M. and D.R. Keeney (1975). Behavior and Phytotoxicity of Inorganic Arsenicals in Soils. *Arsenical Pesticides*. E. A. Woolson. Washington, D.C., ACS: 35-52.

Blaylock, et al., Enhanced Accumulation of PH in Indian Mustard by Soil-Applied Chelating Agents, *Environ.Sci Technol*. 1997, 31, p 860-865.

Pickering, et al., Reduction and Coordination of Arsenic in Indian Mustard, *Plant Physiology*, Apr. 2000, vol. 122, p 1171-1177.

Noctor, et al., Glutathione: Biosynthesis, Metabolism and Relationship to Stress Tolerance Explored in Transformed Plants, *Journal of Experimental Botany*. vol. 49, No. 321, p 623-647.

Ho, et al., Potential Use of a Roadside Fern (Pteris VittaT-A) to Biomonitor Pb and Other Aerial Metal Deposition, *Bull. Environ. Contam. Toxicol.* (1985) 35:430-438.

* cited by examiner

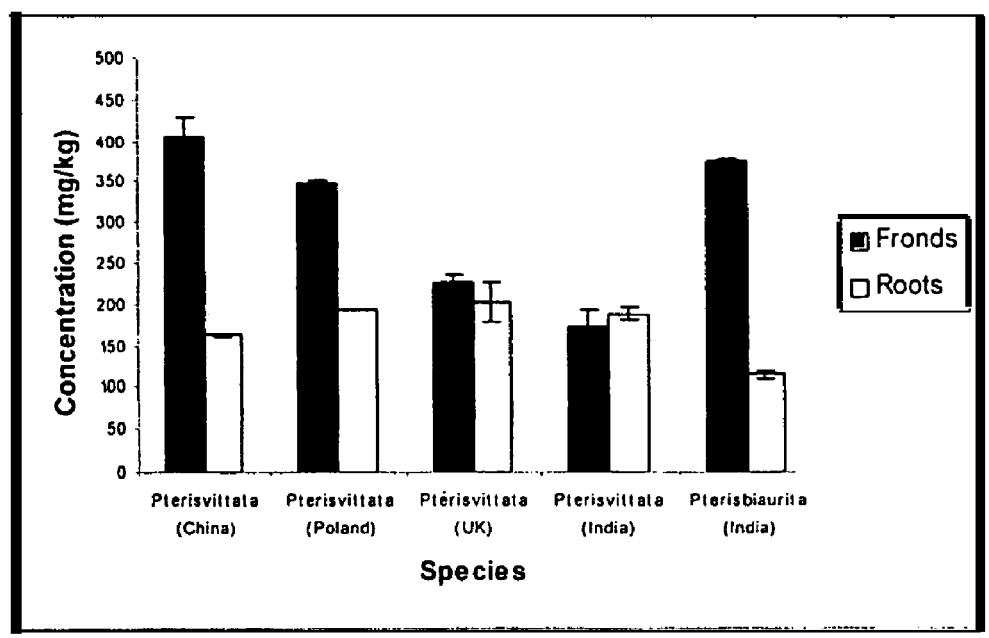
Fig.1. Arsenic concentrations in *Pteris* ferns from different locations after exposing to 300 μM arsenate for 3d.

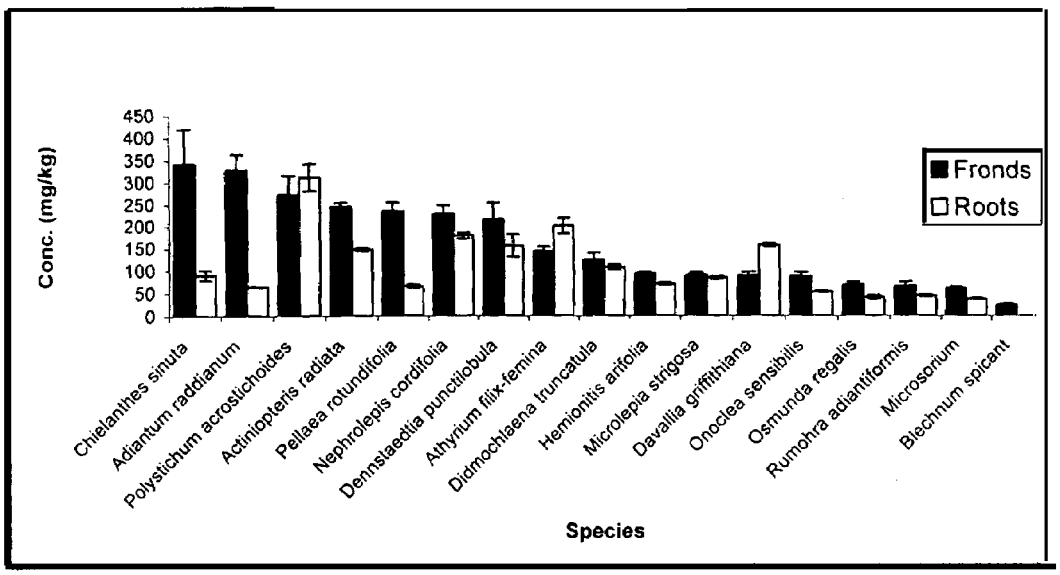
Fig.2. Arsenic concentrations in 17 non-*Pteris* ferns after exposing to 300 μM arsenate for 3d.

CONTAMINANT REMOVAL BY ADDITIONAL FERNS

This invention is a Continuation-In-Part (CIP) of U.S. Ser. No. 10/825,993 filed Apr. 16, 2004, which is a Continuation-In-Part (CIP) of U.S. Ser. No. 10/756,237 filed Jan. 12, 2004, which is a Continuation-In-Part (CIP) of U.S. Ser. No. 09/948,969, filed Sep. 7, 2001, now abandoned, which is a Divisional application of U.S. Ser. No. 09/546,941 filed Apr. 11, 2000, now U.S. Pat. No. 6,302,942, which is a Continuation-In-Part (CIP) of U.S. Ser. No. 09/471,566 filed Dec. 23, 1999, now U.S. Pat. No. 6,280,500, which claims the benefit of priority from U.S. Provisional Application Ser. No. 60/129,203, filed Apr. 14, 1999.

FIELD OF THE INVENTION

This invention relates to compositions and methods of phytoremediation using various fern plants for removing contaminated substances such as arsenic, from sites containing polluted soils and waters and airborne substances such as those found with waste water, ground water, surface water, combinations thereof via phytoremediation through the soil and/or water, and by using excised (cut-off fronds) plant parts.

BACKGROUND OF THE INVENTION

Arsenic Chemistry and Toxicity

Arsenic is a major contaminant of soils, sediments, wastes, and water in the United States and in foreign countries. Contamination of soils results from, for example, pesticides application and pressure-treated woods. Not only is arsenic a prevalent contaminant but it is also particularly dangerous because it is a known carcinogen. Currently there is no cost effective and efficient way to clean up sites contaminated with arsenic.

The use of arsenic in agricultural and industrial processes has resulted in numerous contaminated sites in Florida. During the early part of the 20$^{th}$ century, arsenic was commonly used as an insecticide component to control disease-carrying ticks on southern cattle so that Florida cattlemen could sell to the northern cattle markets. Arsenic, typically in the form of arsenic pentoxide, was also used in conjunction with copper sulfate and sodium or potassium dichromate as a wood preservative which is known as the copper/chromium/arsenic wood preservative process (CCA). With both of these processes, the risk of soil contamination from spills and leaks was great. The arsenic level at many of these sites is currently higher than 600 mg/kg even after years of idleness. The typical concentration range in soil is between 0.1 to 40 mg/kg, with a mean concentration of 5–6 mg/kg. The typical range of arsenic in Florida soils is 0.01 to 50.6 mg/kg.

In most soil systems, arsenic is present in many forms of which arsenate is typically the dominant one. In this form, it has properties very similar to phosphate including the formation of insoluble salts with cations and sorption by soil constituents. Because arsenic has a wide range of oxidation states (−3, 0, +3, and +5) it has the ability to form many types of organic and inorganic complexes. At high pH ranges, typically 7 to 9, the arsenic in soils predominantly consists of complex oxyanions of As(V), such as $AsO_2^{-1}$, $AsO_4^{-3}$, $HAsO_4^{-2}$, and $H_2AsO_4^{-1}$. In soils with low pH and low Eh, the predominant forms of arsenic are the arsenite ($H_3AsO_3$).

Although arsenic is commonly found in all natural systems at minute levels, it can be very toxic to both plants and animals at higher concentrations. The toxic effects of arsenic have been known for some time. The exposure of animals to arsenic is second in toxicity only to lead (Pb) for many farm and household animals. Most cases of arsenic poisoning in animals occur in bovine and feline species as a result of contaminated feed supplies. Other species that are affected are forage-eating animals, such as horses and sheep, that encounter fields that may have been treated with arsenic pesticides. The toxic effects of arsenic to humans and animals can be related to the interactions that occur within the cells of poisoned individuals, especially the mitochondria.

Phytoextraction

Arsenic contamination in the environment is of concern due to its biological activities as a teratogen, carcinogen, and mutagen as well as its detrimental effects on the immune system. Due to the concern expressed over arsenic contaminated sites, various remediation techniques have been developed. Methods for remediating arsenic contaminated sites can be performed in situ and ex situ and have varying degrees of complexity, effectiveness, and cost. Due to the lack of effective technologies and the costs associated with the excavation and landfilling of the soil materials efforts to remediate these arsenic contaminated sites have been minimal. These remediation methods can be divided into three groups: chemical, physical, and biological remediation methods.

One of the biological remediation techniques is phytoremediation, more specifically phytoextraction. Phytoextraction attempts to remove contaminants from the rhizosphere through plant uptake and the contaminants are accumulated in roots, leaves and/or stems. The plant materials are then harvested and the contaminants reclaimed from the plant biomass or the materials are disposed of at a hazardous waste facility. Phytoextraction is an organic, low input, and solar energy powered remediation technique that is applicable to sites with surface and low to medium levels of contamination. The ideal plant for phytoextraction must be able to tolerate high levels of the element in root and shoot cells. Plants used for phytoextraction must have the ability to translocate the contaminant from roots to shoots at high rates. For most plants, root concentrations are much higher than shoot concentrations, but in hyperaccumulators, shoot metal concentrations exceed root.

There have been several reports of arsenic accumulating plants; on mine wastes from various sites in the United Kingdom; on smelter wastes in northeast Portugal and near a copper mine site in northern Peru. Porter and Peterson (1975) reported that *Jasione montana, Calluna vulgaris, Agrostis tenuis* and *Agrostis stolonifera* collected from highly arsenic polluted sites in the UK contained 6640, 4130, 3470 and 1350 µg As g$^{-1}$ dry mass, respectively. De Koe (1994) found *Agrostis castellana* from the gold mines in Portugal reached arsenic values of 1900 mg kg$^{-1}$ but was still in the range reported by Porter and Peterson (1975) for other *Agrostis* species. The highest As concentration previously reported in plants was for the grass *Paspalum racemosum*, which contained up to 5,280 µg As g$^{-1}$ in their dead leaves.

Currently, many plants have been identified that can be utilized to remediate soil and water systems contaminated with metals, metalloids, petroleum constituents, pesticides, and industrial wastes. Also, many plant species have been identified that accumulate lead, selenium, nickel, zinc, and other metals. For example, U.S. Pat. Nos. 5,364,451 and 5,711,784 describe phytoremediation of metal-contaminated soils. For the remediation of contaminated sites contaminated with metals, phytoextraction can be an attractive option. Phytoextraction is the process of removing a contaminant from a system via plant roots for remediation purposes.

*Pteris vittata*

There are more than 400 hyperaccumulators identified in different taxa mostly belong to nickel, cadmium, and zinc (Brooks, 1998). Recently, Ma et al. (2001) discovered the first known vascular plant, a fern, (*Pteris vittata* L.), commonly known as Chinese brake fern that hyperaccumulates arsenic. *Pteris vittata* took up phenomenal concentrations of arsenic (as high as 2.3%) from soil and allocated most of it to the aboveground fronds (up to 90%) for final storage (Tu and Ma, 2002). Most importantly, the hyperaccumulation of arsenic was accompanied by an increased biomass of the aboveground plant parts (Ma et al., 2001; Tu and Ma, 2002). Other desirable characters permitting *P. vittata* as an ideal plant for phytoremediation include its perennial growth habit, disease and pest resistance, fast vigorous growth, and diverse ecological niche with high pH.

Arsenic hyperaccumulation largely depends on the root geometry and morphology since root systems that have higher ratios of surface area to volume will more effectively explore a larger volume of soil. *Pteris vittata* develops an extensive network of root system enriched with root hairs. Bondada and Ma (2002) reported the root length and density of the fern grown in arsenic contaminated soil were 363 µm and 9 µm$^{-2}$, substantially greater than the length and density of *P. vittata* grown in cadmium contaminated media (Gupta and Devi, 1994) indicating that arsenic may have stimulatory effect of root hair development in the fern. Since hyperaccumulation of metals appears to be driven by increased rates of root uptake, the dense population of root hairs in the fern, in addition to increasing absorptive surface, may contribute to increased rates of arsenic uptake by increasing number of transporters per gram fresh weight. Even though significant progress has been made in understanding the physiological basis of plant tolerance to arsenic, there remains considerable uncertainty about the mechanism in *P. vittata*. Tu et al. (2002) reported that *P. vittata* roots with low arsenic concentration and high phosphorus: arsenic ratio exhibited increased affinity to, and high influx rate of arsenic.

*Pteris vittata* has the remarkable ability to hyperaccumulate arsenic in the fronds, with frond concentrations reaching levels up to 100 fold greater than soil concentrations. This ratio is held both for uncontaminated (6 mg kg$^{-1}$ As) and highly contaminated (1,500 mg kg$^{-1}$ As) soils. The fern is capable of taking up of a range of inorganic and organic arsenic species including arsenate, arsenite and MMA. In the fern, arsenic is mostly present in inorganic forms, with 47–80% of the arsenic present as arsenite in the fronds.

Arsenic Uptake Other than Roots

Studies dealing with uptake of heavy metals by hyperaccumulators focused primarily on metal uptake from the soil solution via the root system. This is because most of the heavy metals reside in the soil system, and after uptake, they are often confined in the roots. Other than the roots, the aerial organs such as leaves are also capable of absorbing soluble heavy metals if they receive it in aqueous form (Lepp, 1975). Metals such as Cd, Zn, Cu, and Pb enter the leaf through foliar pathways, however, their entry through the leaf cuticle into leaf varied depending upon metal species (Little and Martin, 1972; Greger et al., 1993). Arsenic, a highly soluble metalloid, is normally applied in combination with other compounds as a toxin for pest mortality (Handson, 1984). In the past, however, foliar sprays of arsenic had been used to improve juice quality in citrus (Procopiou and Wallace, 1979) indicating that arsenic could gain entry into the plants through the foliar pathways.

Since different biochemical reactions occur in different parts of a plant, excised plant, such as shoots, stems, leaves and roots, have been widely used to characterize the absorption and metabolism of nutrients and chemicals as well as heavy metals in plants (Facanha and Okorokova-Facanha, 2002; Waldrop et al., 1996; Zhang and Taylor, 1991). We have examined the uptake of different As species (organic/inorganic and arsenate/arsenite) by *P. vittata* and As speciation in its plant biomass (Ma et al., 2001; Tu and Ma, 2002). However, there are many questions remain unanswered, such as where As reduction occurs in the plant, i.e. roots, fronds or both, and how P affects plant As uptake and reduction. The hypotheses were that both P and As species could affect plant As uptake, speciation and thiol formation in *P. vittata*, and such effects could be effectively characterized by use of excised parts of *P. vittata*. It was expected that use of excised parts of *P. vittata* to characterize As uptake, speciation and thiol formation would shed light on its mechanisms of As hyperaccumulation.

Although live biological systems work well for low concentrations, they cannot survive the high levels that are found in heavily contaminated areas and industrial effluents. The use of non-living biomaterial containing metal-binding compounds would have the advantage of not requiring care and maintenance as well as being useful in remediating areas with high levels of contaminants that would otherwise kill live systems. A wide variety of biomass, including bacteria, fungi, algae and higher plants have been tested as adsorbents to clean up metals in contaminated aqueous environments. Live or dead cultured cells of a higher plant, *Datura innoxia* Mill have been used to remove Ba$^{2+}$ from solution. Aquatic ferns, *Azolla filiculoides* Lam and *Azolla pinnata* R.Br have also been reported to accumulate metals and can be used as biosorbents in remediating industrial effluents. A large number of aquatic plants were reported to be utilized for water purification and removing heavy metals from water. However, in aquatic plants, characterized by small size and slow growing roots, the efficiency of metal removal seems to be low. High water content in these plants renders their drying, composting and incineration processes complicated.

Terrestrial plants develop longer, fibrous root systems with root hairs, which creates a high surface area for effective absorption, concentration or precipitation of toxic metals from polluted media. An assessment of removal of toxic metals from solution by phytomass of *Quercus ilex* for a wide range of metals such as Cr, Ni, Cu, Cd and Pb indicated high sorption capacity of the phytomass for Ni and potential use as a biosorpent agent in contaminated aqueous media.

Prior to the subject invention, there has been no plant species identified that can enrich large quantities of arsenic into its biomass from contaminated soils, with arsenic concentration in plant being much greater than that in the soil. Also, prior to the subject invention there has been no report of the use of fern plants in phytoremediation. In addition, prior to the subject invention there has been no report of fern-based phytoremediation using the following methods:, e.g. foliar application, excised plant parts and dry or fresh plant biomass.

SUMMARY OF THE INVENTION

A primary objective of the subject invention is to provide for compositions and methods of using *Pteris* and non-*Pteris* fern plants for removing pollutants and contaminants such as arsenic, from water environments through phytoremediation.

A secondary objective of the invention is to provide for compositions and methods of using *Pteris* and non-*Pteris* fern plants for removing pollutants and contaminants such as arsenic, from soil environments through phytoremediation.

A third objective of the invention is to provide for compositions and methods of using *Pteris* and non-*Pteris* fern plants for removing pollutants and contaminants such as arsenic, from water and soil environments through phytoremediation.

A fourth objective of the subject invention is to provide for using fronds of *Pteris* and non-*Pteris* fern plants to remove pollutants and contaminants by foliar application, where the pollutants/contaminants are removed through surface applications on the fronds of the *Pteris* and non-*Pteris* fern plants.

A fifth objective of the subject invention is to provide for using excised portions of *Pteris* and non-*Pteris* fern plants such as excised leaflets to remove pollutants and contaminants by placing the excised portions (cut-off fronds) in contact with the pollutants and contaminants.

The subject invention pertains to the identification of *Pteris* and non-*Pteris* fern plants, which are able to extract pollutants from contaminated materials. In a preferred embodiment, the pollutant is arsenic.

Pollutants can be removed from materials including, but not limited to, soils, sediments, wastes, and water, and combinations, thereof by the plants of the subject invention which accumulate the pollutants in the biomass of the plant. This is advantageous because these plants can be used to efficiently remediate contaminated materials.

In a preferred embodiment the subject invention provides a method for phytoremediating arsenic-contaminated sites wherein arsenic accumulating fern type plants remove arsenic from the contaminated materials. Specifically exemplified herein is the use of *Pteris vittata* (Chinese Brake fern).

The fern plants of the subject invention accumulate arsenic in very high concentrations. The plant leaves, stems, and/or roots can then be harvested and readily disposed of, thereby reducing the arsenic content of the contaminated site. Alternatively, arsenic can be recovered from the harvested plants.

The fern plants of the subject invention have many advantageous characteristics for use in phytoremediation. For example, these plants are extremely efficient in extracting arsenic from soils (extremely high arsenic enrichment factor), they grow in many environments, they grow quickly producing a large biomass and they reproduce easily. Also, advantageously, they are perennials which do not need to be replanted each year.

In addition to efficient root uptake, the fern plants can also be used to remediate arsenic contaminated water via foliar application (arsenic uptake through leaves in live plants). Additionally, arsenic uptake can take place in stem portions and spore(s) of the live plant.

Another embodiment includes using excised plant portions to remove pollutants and contaminants. For example, floating excised fern leaflets in water (leaflets are detached from a live plant), can remove arsenic type pollutants.

Further objects and advantages of this invention will be apparent from the following detailed description of the presently preferred embodiments, a detailed description of the following examples and the accompanying drawing.

BRIEF DESCRIPTION OF THE FIGURES

FIG. 1 is a graph of arsenic concentrations in *Pteris* ferns from different locations after exposing the ferns to approximately 300 µM arsenate for approximately 3 days.

FIG. 2 is a graph of arsenic concentrations in 17 non-*Pteris* ferns after exposing the ferns to approximately 300 µM arsenate for approximately 3 days.

DETAILED DESCRIPTION OF THE PREFERRED EMBODIMENTS

Figure 3A:
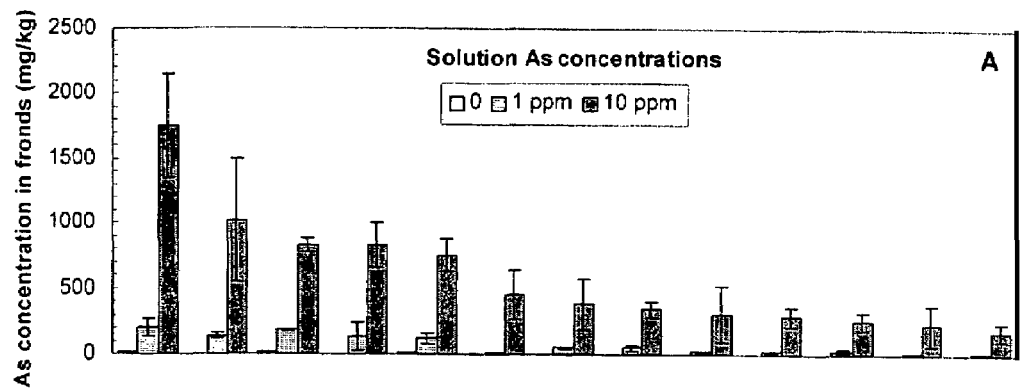
FIG. 3A is a graph of arsenic concentration in various fronds of *Pteris* and on-*Pteris* plants in mg/kg.
Figure 3B:
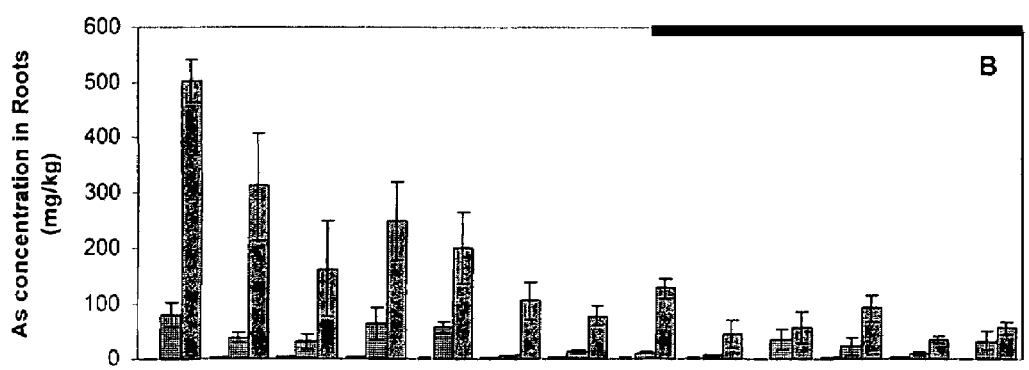
FIG. 3B is a graph of arsenic concentration in various Roots of the plants of FIG. 3A in mg/kg.
Figure 3C:
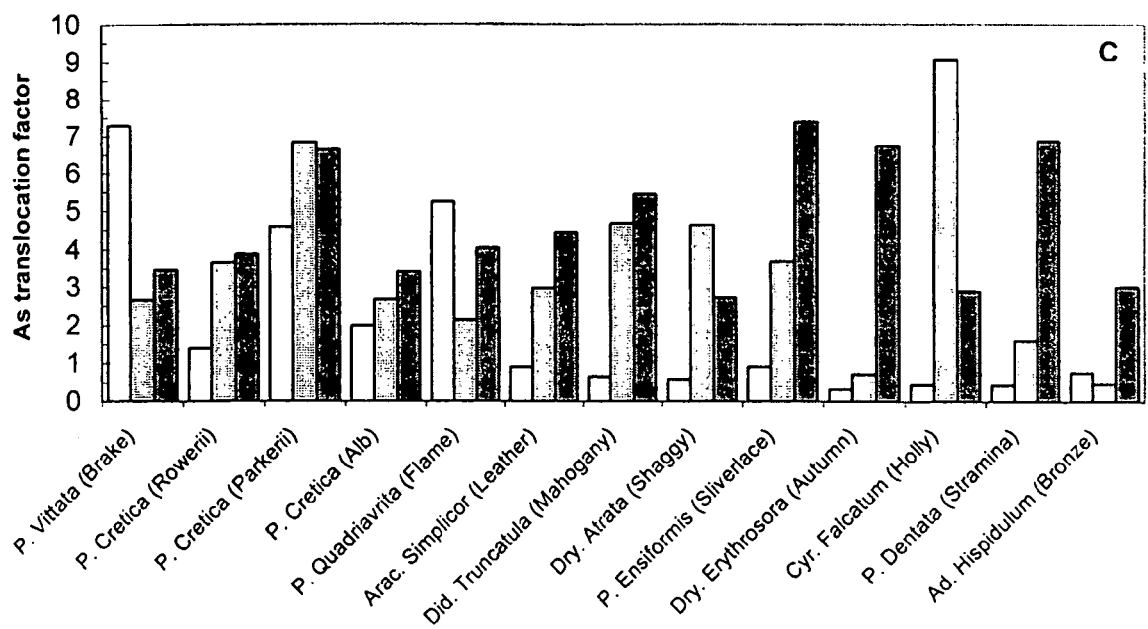
FIG. 3C is a graph of arsenic translocation factor of the plants of FIGS. 3A–3B.

Before explaining the disclosed embodiments of the present invention in detail, it is to be understood that the invention is not limited in its application to the details of the particular arrangements shown since the invention is capable of other embodiments. Also, the terminology used herein is for the purpose of description and not of limitation.

The subject invention pertains to the identification of plants that accumulate arsenic in very high concentrations. These plants can be used to remediate arsenic contaminated sites. Preferably, the plants which are used in the remediation methods of the subject invention are fern type plants. With the teachings provided herein, the person skilled in the art could, for the first time, utilize fern plants to remove various pollutants. The inorganic pollutants may be bonded to, or otherwise chemically associated with, organic or inorganic compound(s). The pollutants may be, for example, copper, chromium, or phosphorus. Preferably, arsenic is removed. The metals may be, for example, lead, gold, selenium, copper, cadmium, chromium, nickel, or zinc. Preferably, arsenic is removed. The materials from which the pollutant is removed may be any contaminated materials and can exist as liquid form, for example, surface and groundwater. The examples of waters include but not limited to groundwater, surface water, runoff, or waste water.

In a preferred embodiment, the method of the subject invention involves contacting a fern plant with arsenic-containing material and maintaining the plant in the environment under conditions sufficient for the plant to accumulate arsenic from the material. The plant is maintained in the site for a period of time and under conditions sufficient for the plant to accumulate arsenic in the stems, leaves and/or roots. The plant may be harvested from the site and disposed of.

Arsenic "accumulating" fern plants refer to the ability of the fern plants described herein to perform one, or more, of the following activities: (i) transporting arsenic from liquid into the roots and/or other tissues; (ii) physical and/or chemical sorption of arsenic to the plant biomass; and (iii) prevention or inhibition of leaching of arsenic from the contaminated material. In a preferred embodiment arsenic is transported into the leaf and/or stem tissue of the fern.

As used herein, reference to "fern plants" includes the *Pteridophytes* (true fern). Most fern plants are sporophytes which reproduce by means of spores. Fern plants typically produce masses of sporangia either on the underside of vegetative leaves or on specialized leaves that function only as reproductive structures. Specifically exemplified herein are fern plants of the orders Pteridales and Aspidiales and the families of Pteridaceae, Adiantaceae, Aspleniaceae, Dryopteridaceae, and Oleandraceae. Specifically exemplified genera are *Adiantum, Asparagus, Asplenium, Cyrtomium, Didymochlacna, Dyropteris, Nephrolepis, Pteridium, Rumohra*, and *Pteris*. The *Pteris* ferns are also known as Chinese brake ferns. The specific examples of the *Pteris* ferns are *P. cretica mayii, P. cretica parkerii, P. cretica albo-lineata*, and *P. vittata*.

Fern plants useful according to the subject invention can be readily identified by those skilled in the art. Useful guides to fern plants are readily available and include, for example, Lakela, Olga and Robert W. Long: "*Ferns of Florida*", An Illustrated Manual and Identification Guide" [1976], Banyan Books, Miami, Fla.); Jones, David L. (Encyclopedia of Ferns [1987], Lothian Publishing Company PTY LTD); and Snyder, Jr., Lloyd H. and James G. Bruce (Field Guide to the Ferns and Other *Pteridophytes* of Georgia" [1986] The University of Georgia Press).

Advantageously, the fern plants used in the present invention: (a) can be grown to high biomass; (b) are adaptable for growth in various agro-climatic conditions; (c) are adaptable to high-density culture; (d) are amenable to genetic manipulation by crossing, selection, mutagenesis and/or gene transfer. The excellent remediation properties presented herein are under field conditions and can be improved by optimization of field conditions as described herein, or by performing the remediation process in a controlled environment such as in a greenhouse.

The conditions which can be manipulated to optimize performance in a given system include, pH, nutrients, water content, sunshine/shade, and amendments including chelators, organic amendments and inoculation of microorganisms. Optimization parameters, such as addition of nutrients (to support healthy plants) and amendments (to increase pollutant availability), apply to all fern plants, whereas others apply only to *P. vittata*. The pH may be adjusted, for example, to be greater than 6.5 using liming materials such as limestone, dolomite, hydrated lime, burn lime, alkaline industrial wastes (e.g. ash and sludge), and phosphate rock.

Essential macronutrients and micronutrients may also be applied including, for example, N, P, K, Ca, Fe, Mn, and Cu. *Pteris vittata* is a hardy plant, which shuns shade and revels in sunshine, and it requires free drainage but appreciates watering during dry periods. Additionally, chelators such as ethylene diamine tetraacetic acid (EDTA), dithylenetriaminpentaacetic acid (DTPA), nitrilotriacetic acid (NTA), citric acid, and oxalic acid can be applied. Acidic environment (pH<6) and too much salt (over fertilization) can be detrimental to fern plant growth. The fern plants specifically exemplified herein are highly useful in removing arsenic from contaminated waters.

In an alternative embodiment, the fern plants can be genetically manipulated to improve and/or expand their phytoremediation characteristics. See U.S. Pat. No. 6,005,092 to Shoseyou et al, which is incorporated by reference. Such characteristics may be for example the growth rate of the fern plants, the uptake rate of arsenic, and the hardiness of the plant. The genetic manipulation may be through, for example, traditional breeding techniques, mutagenesis, and/or genetic engineering.

In a related embodiment, the genetic components responsible for the ability of fern plants to accumulate arsenic can be identified, isolated, and, if desired, transferred to another plant species thereby conferring on the transformed plant the ability to accumulate arsenic in useful levels. Alternatively, microorganisms and/or their genetic components involved in the arsenic removal process can be isolated and utilized.

In a specific embodiment, the subject invention provides an arsenic-accumulating fern plant. *Pteris vittata* has been shown to accumulate up to and exceeding approximately 540 mg/kg arsenic (dry weight) in its fronds. The arsenic concentrations in the water where the plant has been studied was approximately 20 mg/L. Thus, this plant has an extraordinary capability to enrich nearly approximately 27 times more arsenic in its plant tissue than in the contaminated water. Advantageously, the fern plants of the subject invention remove contaminants from water having even low concentrations of pollutants. This is important for the process of the subject invention to lower the concentration of contaminants to an acceptable level.

The preferred methods of the invention involve growing or using one or more members of these plants under conditions sufficient for them to accumulate arsenic in their biomass. The term "arsenic" also includes mixtures, or compounds, comprising arsenic and organic or inorganic compounds.

The arsenic-containing environment into which these plants are introduced is not intended to limit the scope of the invention. That is, as long as the environment can sustain growth or presence of fern plants, the environment can be purely aquatic environments (i.e., hydroponic culture). Advantageously, fern plants can be grown in the sun or in the shade, and in either moist or dry environments. For example, the subject invention may be utilized in wetlands, and the like. The pH can be as high as about 6 to about 8 or even higher.

The arsenic-accumulating fern plants suitable for the present methods extract arsenic from the environment into the biomass of the fern plant. Preferably, the plants will translocate the arsenic from the roots into the shoots (i.e., the aboveground portions of the plant). The rates of accumulation can vary depending on a variety of factors, including the total arsenic concentration, pH, planting density, and fertilizer use. With the teachings provided herein, the skilled artisan can readily select the preferred conditions for a particular application.

Generally, accumulation by the preferred fern plants can be as high as approximately 100-fold or more above the levels present in the environment. The most preferred fern plant members accumulate several percent of arsenic as dry weight of shoot biomass. Shoots can then be harvested. The ability of the plants of the present invention to accumulate arsenic in the shoots is important because the shoots represent the harvestable (i.e., aboveground) biomass. However, any portion of the plant is potentially harvestable. For example, leaves, stems, fronds and roots may be harvested from fern plants.

In addition to highly contaminated soil, fern plant samples were also collected from uncontaminated sites, with arsenic concentrations ranging from approximately 0.5 to approximately 7.6 mg/kg. The arsenic concentrations in the frond (above-ground biomass) of these plants ranged from approximately 12 to approximately 64 mg/kg, with a maximum arsenic enrichment factor of approximately 136. This clearly demonstrates that the fern plants of the subject invention accumulate arsenic from soils containing high as well as low arsenic levels.

Thus, the arsenic enrichment factor of fern plants is observed under natural growing conditions in contaminated as well as uncontaminated soils. The person skilled in the art, having the benefit of the current disclosure could optimize conditions for growth of the plants and uptakes of the pollutants. The uptake reported here is under conditions in the field and could be increased in an appropriately controlled environment such as a greenhouse.

Arsenic concentrations in common plants range from approximately 0.01 to approximately 5 mg/kg, with an average of approximately 2.5 mg/kg. Thus, the fern plants of the subject invention accumulate as much as approximately 3,000 times more arsenic than the average of common plants without suffering from arsenic toxicity. This is extremely unusual for a plant since arsenic has been and still is being used as a herbicide to control weeds.

The fern plants of the subject invention are highly advantageous for use in methods to remove arsenic from contaminated waters. These fern plants also have a relatively large biomass; for example, these fern plants can produce a frond that is approximately 30 to approximately 90 cm in length, with blades of approximately 25 to approximately 60 cm long and approximately 13 to approximately 25 cm wide. Also, fern plants can be easily reproduced in tens of thousands from just one plant. Once planted in an arsenic contaminated soil, the fern plants of the subject invention come back every year because they are perennial plants, i.e., the fern plants can be harvested season after season until the site is cleaned up without reseeding or replanting.

In a specific embodiment, the subject invention concerns an arsenic accumulating $P.$ $vittata$. The arsenic concentration in the water where samples was collected was approximately 10 mg/L, with the highest arsenic concentration in the fronds being approximately 1,666 mg/kg. Hence, the arsenic concentration in the fern can be approximately 167 times greater than that in water. This plant is highly advantageous for extracting arsenic from arsenic contaminated water, including groundwater.

The arsenic accumulating fern plants of the subject invention can be used to remediate tens of thousands of arsenic contaminated waters nationwide and around the world. When the fern plants are harvested, the arsenic, phosphorous or other metal can be recovered or disposed of using methods know to those skilled in the art. The disposed or recovery step may include, for example, microbial treatment, chemical treatment, incineration, treatment with other plants, etc. These methods may further include the use of gasifiers.

The specific applications that this technique can be applied to arsenic contaminated environments include the following:

1. Cleanup arsenic contaminated groundwater or surface water;

Arsenic contaminated groundwater or surface water can be pumped up to irrigate the field where the fern plants grow to allow arsenic to be taken up by the fern plants and cleanup the groundwater; Arsenic uptake by the fern is through both roots and fronds.

2. Cleanup waters contaminated with both organics and arsenic.

Both Fem plants (uptake arsenic and phosphorus) and poplar trees (help degrade organic contaminants) can be planted in the field to clean up co-contaminated groundwater;

3. Cleanup waters contaminated with both lead and arsenic.

Both fern plants (uptake arsenic and phosphorus) and India mustard (uptake lead) can be planted in the field to clean up co-contaminated waters;

4. Treat wastewater.

Fem plants can be grown in a field where wastewater can be used for irrigation to remove arsenic from the wastewater.

In a specific embodiment the subject invention concerns a method of phytoremediating contaminated waters comprising cultivating fern plants in the materials containing contaminants under conditions sufficient to permit the fern plants to accumulate contaminants from the materials in the biomass of the fern plants such that the contaminants are at least approximately 100 mk/kg of dry biomass of the fern plants. The fern plants can then be harvested and the contaminants recovered from the biomass. Preferably, the materials are conditioned to an optimized nutrient level to increase plant biomass and contaminants bioavailability. Contaminants include both organic and inorganic pollutants that are of environmental concern and include, but are not limited to, arsenic, phosphorous and other trace elements and heavy metals.

Arsenic Removal in Pteris Ferns from Different Locations and Non Pteris Ferns

EXPERIMENT ONE (1)

Contaminant Removal by Phytoremediation Through Roots and Fronds

This experiment was conducted to screen different fern plants for their ability in arsenic accumulation. This include both $Pteris$ and non-$Pteris$ ferns. The $Pteris$ ferns included $P.$ $biaurita$ (from India) and four accessions of $P.$ $vittata$ (from UK, China, India, and Poland), which were germinated in our laboratory using spores. The non-$Pteris$ ferns included 1 7 species, which were obtained directly from Casa flora, a nearby nursery in Apopka, Fla. They were $Actiniopteris$ $radiata$, $Adiantum$ $raddianum$, $Athyrium$ $filix$-$femina$, $Blechnum$ $spicant$, $Chielanthes$ $sinuta$, $Davallia$ $griffithiana$, $Dennstaedtia$ $punctilobul$, $Didmochlaena$ $truncatula$, $Hemionitis$ $arifoli$, $Microlepia$ $strigosa$, $Microsoorium$ $diversifolium$, $Nephrolepis$ $cordifolia$, $Onoclea$ $sensibilis$, $Osmunda$ $regalis$, $Pellaea$ $rotundifolia$, $Polystichum$ $acrostichoides$, and $Rumohra$ $adiantiformis$.

There were no visual symptoms of arsenic toxicity in all fern plants after being exposed to approximately 300 µM. (22.5 mg $L^{-1}$) of arsenate for three days. All species of $Pteris$ fern screened in this study, including four accessions of $P.$ $vittata$, and $P.$ $biaurita$ were effective in arsenic accumulation as shown in FIG. 1. Arsenic concentrations were approximately 173 to approximately 404 mg $kg^{-1}$ in the fronds (aboveground biomass) and approximately 115 to approximately 202 mg $kg^{-1}$ in the roots.

Among the four accessions of $P.$ $vittata$, Chinese accession had the highest levels of arsenic in the fronds, with the arsenic levels exceeding approximately 400 mg $kg^{-1}$ of dry weight. The Indian plants accumulated the least amount of arsenic in the fronds, i.e., approximately 173 mg $kg^{-1}$. Among the five $Pteris$ ferns, $P.$ $biaurita$ was the second best in arsenic accumulation. Based on arsenic accumulation, all five $Pteris$ ferns can be considered as potential arsenic hyperaccumulators.

Referring to FIG. 2, the non-$Pteris$ fern species varied greatly in their ability to accumulate arsenic. Arsenic concentrations in the 17 non-$Pteris$ ferns were approximately 24 to approximately 341 and approximately 38 to approximately 310 mg $kg^{-1}$ in the fronds and roots, respectively. The highest arsenic concentration in the fronds was measured in *C. sinuta*, i.e. approximately 341 mg kg$^{-1}$. The lowest level was recorded in *B. spicant*, i.e. approximately 24.3 mg kg$^{-1}$. Using the lowest arsenic accumulation by *Pteris* fern as an arbitrary value, i.e. approximately 173 mg As kg$^{-1}$, to screen non-*Pteris* ferns, seven ferns were potential arsenic hyperaccumulators. They were *C. sinuta, A. raddianum, P. acrostichoides, A. radiate, P. rotundifolia, N. cordifolia*, and *D. punctilobula* with a minimum of approximately 215 mg As kg$^{-1}$ in the fronds.

EXPERIMENT TWO (2)

Contaminant Removal by Phytoremediation Through Roots and Fronds

For this experiment, six *Pteris* (*P. Cretica* Rowerii, *P. Cretica* Parkerii, *P. Cretica* Albo-lineata, *P. Quadriavrita, P. Ensiformis* and *P. Dentata*) and six non-*Pteris* (*Arac. Simplicor, Did. Truncatula, Dry. Atrata, Dry. Erythrosora, Cyr. Falcatum*, and *Ad. Hispidulum*) ferns species in addition to *Pteris vittata* were exposed to approximately 0, 1 and approximately 10 mg L$^{-1}$ sodium arsenate for approximately 14 days in hydroponic systems.

*Pteris vittata* was the most efficient in arsenic accumulation, followed by *P. cretica*, with the *Pteris* ferns being more efficient than the non-*Pteris* ferns. When exposed to approximately 10 mg L$^{-1}$, arsenic concentrations in fronds and roots of *P. vittata* were approximately 1748 and approximately 503 mg kg$^{-1}$. The corresponding numbers for the *Pteris* fern were approximately 816 and approximately 316 mg kg$^{-1}$, and non-*Pteris* ferns approximately 117 and approximately 32.7 mg kg$^{-1}$.

However, not all *Pteris* ferns were efficient in accumulating arsenic but none of the non-*Pteris* ferns were efficient either with the highest arsenic accumulation of approximately 452 mg kg$^{-1}$. The fact that the background arsenic concentrations in the fronds were highly correlated with those in the fronds after exposed As ($r^2$=approximately 0.76 to approximately 0.87) can suggest that they can be used as a preliminary tool to screen potential arsenic hyperaccumulators.

Based on arsenic accumulation in the fronds, five *Pteris* ferns can be potentially classified as arsenic hyperaccumulator, and they are *P. vittata, P. Cretica Rowerii, P. Cretica Parkerii, P. Cretica Albo-lineata*, and *P. Quadriavrita*.

EXPERIMENT THREE (3)

Contaminant Removal Through Cut-Off Plant Parts (Cut-Off Fronds)

Twelve fern species were used in this experiment including two *Pteris* ferns (*P. vittata* and *P. ensiformis* and 10 non-*Pteris* fern species (*Nephrolepis cordifolia* "Duffii, *Nephrolepis exaltata* "Delilah, *Polystichum polyblepharum* "Tassel fern", *Didynachlaena truncatula* "mahogany", *Dryopteris atrara* "shaggy shield", *Dryopteris flixmas, Davalia trichomanoides* "rabbit foot", *Adiantum hispidulum* "bronze venus ", *Nephrolepis exaltata* "emina ", and *Adiantum hispidulum* "rosy maiden hair"). The fronts of 12 ferns were cut into approximately 1-cm pieces, which were put into approximately 10 mg L$^{-1}$ AsIII or AsV solution and shaken for 24 hours. Arsenic being a general term, that can include both arsenate (AsV)-oxidized form and asrenite (AsIII)-reduced form.

Though none of the other ferns was as effective as *P. vittata*, several were effective in reducing arsenic concentrations in the solution. Four fern species, *Polystichum polyblepharum, Dryopteris flixmas, Adiantum hispidulum*, and *Adiantum hispidulum*, were effective in reducing AsIII from solution, and two, *Didynachlaena truncatula* and *Nephrolepis exaltata*, were effective in reducing AsV from solution. These ferns can be potentially classified as arsenic hyperaccumulators.

TABLE 1

The effectiveness of different fern fronds in taking up 10 mg L$^{-1}$ AsIII or AsV after 24 h of reaction.

| | As III | AsV |
|---|---|---|
| *Pteris vittata* | 28.7 | 2.6 |
| *Pteris ensiformis* | 14.5 | 3.4 |
| *Nephrolepis cordifolia* "Duffii" | 5.5 | 0.6 |
| *Nephrolepis exaltata* "Delilah" | 2.4 | 0 |
| *Polystichum polyblepharum* "Tassel fern" | 17.3 | 5.7 |
| *Didynachlaena truncatula* "mahogany" | 4.2 | 20 |
| *Dryopteris atrara* "shaggy shield" | 7.7 | 7.9 |
| *Dryopteris flixmas* | 19.3 | 9.7 |
| *Davalia trichomanoides* 'rabbit foot" | 0 | 6.5 |
| *Adiantum hispidulum* "bronze venus" | 21.2 | 12.9 |
| *Nephrolepis exaltata* "emina" | 13.9 | 16 |
| *Adiantum hispidulum* "rosy maiden hair" | 19.9 | 6.8 |

Other excised plant parts, such as stems, and the like, would also absorb arsenic. A 11 types of other acqueous solution water environments, such as but not limited to wastewater, ground water, surface water, and the like, can use the invention. The invention can work as long as the excised plant parts, such as the leaflets make direct contact with acqueous environments.

The invention embodiments can remove pollutants and contaminants from various environments such as but not limited to water, aqueous solutions, wetlands, soil, air and surrounding atmosphere environment contaminated by herbicide sprays, and the like.

Although the invention embodiments have been described as being used separately, the invention can be practiced by combining any one of the embodiments with another. For example, root uptake of contaminants can be combined with foliar application, and the like.

While the invention has been described, disclosed, illustrated and shown in various terms of certain embodiments or modifications which it has presumed in practice, the scope of the invention is not intended to be, nor should it be deemed to be limited thereby and such other modifications or embodiments as may be suggested by the teachings herein are particularly reserved especially as they fall within the breadth and scope of the claims here appended.

We claim:

1. A process for removing a pollutant through phytoremediation, comprising:
   growing a *Pteris* fern plant selected from the group consisting of a *Pterisvittata* and a *Pterisbiaurita*, in an environment site containing arsenic pollutant; and
   removing a portion of the arsenic through phytoremediation with a live part of the plant.

2. The process of claim 1, wherein the environment site includes : a contaminated ground water, contaminated surface water, or contaminated wetland.

3. The process of claim 1, wherein the environment sites includes: a contaminated soil.

4. The process of claim 1, wherein the live part of the plant includes a root portion of the plant.

5. The process of claim 1, wherein the live part of the plant includes: a leaf portion of the plant.

6. The process of claim 1, wherein the *Pteris* fern plant is a *Pterisvittata*.

7. The process of claim 6, wherein arsenic levels in a frond portion of the plant are at least approximately 400 mg $kg^{-1}$ of dry weight.

8. The process of claim 6, wherein arsenic levels in a root portion of the plant are at least approximately 150 mg $kg^{-1}$ of dry weight.

9. The process of claim 1, wherein arsenic levels in a front portion of the plant are at least approximately 350 mg $kg^{-1}$ of dry weight.

10. The process of claim 1, wherein arsenic levels in a root portion of the plant are at least approximately 200 mg $kg^{-1}$ of dry weight.

11. The process of claim 1, wherein arsenic levels in a front portion of the plant are at least approximately 225 mg $kg^{-1}$ of dry weight.

12. The process of claim 1, wherein arsenic levels in a root portion of the plant are at least approximately 200 mg $kg^{-1}$ of dry weight.

13. The process of claim 1, wherein arsenic levels in a front portion of the plant are at least approximately 175 ma $kg^{-1}$ of dry weight.

14. The process of claim 1, wherein arsenic levels in a root portion of the plant are at least approximately 200 mg $kg^{-1}$ of dry weight.

15. The process of claim 1, wherein the *Pteris* fern plant is a *Pterisbiaurita*.

16. The process of claim 15, wherein arsenic levels in a frond portion of the plant are at least approximately 375 mg $kg^{-1}$ of dry weight.

17. The process of claim 15, wherein arsenic levels in a frond portion of the plant are at least approximately 125 mg $kg^{-1}$ of dry weight.

18. A process for removing a pollutant through phytoremediation, comprising:
 growing a fern plant selected from the group consisting of: *Chielanthes sinuta, Adiantum raddianum, Polystichum acrostichoides, Actiniopteris radiate, Pellaea rotundifolia, Nephrolepis cordifolia,* and *Dennstaedtia punctilobula*, in an environment site containing arsenic pollutant; and
 removing a portion of the arsenic through phytoremediation with a live part of the plant, wherein the part is a root portion or a frond portion.

19. The process of claim 18, wherein the fern plant is *Chielanthes sinuta* and arsenic levels in a frond portion of the live plant are at least approximately 325 mg $kg^{-1}$ of dry weight.

20. The process of claim 18, wherein the fern plant is *Chielanthes sinuta* and arsenic levels in a root portion of the live plant are at least approximately 75 mg $kg^{-1}$ of dry weight.

21. The process of claim 18, wherein the fern plant is *Adiantum raddianum* and arsenic levels in a frond portion of the live plant are at least approximately 350 mg $kg^{-1}$ of dry weight.

22. The process of claim 18, wherein the fern plant is *Adiantum raddianum* and arsenic levels in a root portion of the live plant are at least approximately 60 mg $kg^{-1}$ of dry weight.

23. The process of claim 18, wherein the fern plant is *Polystichum acrostichoides* and arsenic levels in a frond portion of the live plant are at least approximately 275 mg $kg^{-1}$ of dry weight.

24. The process of claim 18, wherein the fern plant is *Polystichum acrostichoides* and arsenic levels in a root portion of the live plant are at least approximately 300 mg $kg^{-1}$ of dry weight.

25. The process of claim 18, wherein the fern plant is *Actiniopteris radiata* and arsenic levels in a frond portion of the live plant are at least approximately 250 mg $kg^{-1}$ of dry weight.

26. The process of claim 18, wherein the fern plant is *Actiniopteris radiata* and arsenic levels in a root portion of the live plant are at least approximately 150 mg $kg^{-1}$ of dry weight.

27. The process of claim 18, wherein the fern plant is *Pellaea rotundifolia* and arsenic levels in a frond portion of the live plant are at least approximately 225 mg $kg^{-1}$ of dry weight.

28. The process of claim 18, wherein the fern plant is *Pellaea rotundifolia* and arsenic levels in a root portion of the live plant are at least approximately 75 mg $kg^{-1}$ of dry weight.

29. The process of claim 18, wherein the fern plant is *Nephrolepis cordifolia* and arsenic levels in a frond portion of the live plant are at least approximately 225 mg $kg^{-1}$ of dry weight.

30. The process of claim 18, wherein the fern plant is *Nephrolepis cordifolia* and arsenic levels in a root portion of the live plant are at least approximately 175 mg $kg^{-1}$ of dry weight.

31. The process of claim 18, wherein the fern plant is *Dennstaedtia punctilobula* and arsenic levels in a frond portion of the live plant are at least approximately 225 mg $kg^{-1}$ of dry weight.

32. The process of claim 18, wherein the fern plant is *Dennstaedtia punctilobula* and arsenic levels in a root portion of the live plant are at least approximately 150 mg $kg^{-1}$ of dry weight.

33. A process for removing a pollutant through phytoremediation, comprising:
 growing a *Pteris* fern plant selected from the group consisting of: *P. vittata, p. Cretica Roweril, P. Cretica Parkerii, P. Cretica Albo-lieata,* and *P. Quadriavrita*, in an environment site containing arsenic pollutant; and
 removing a portion of the arsenic through phytoremediation with a live part of the plant.

34. The process of claim 33, wherein the *Pteris* fern plant is *P. vittata* and arsenic levels in a frond portion of the live plant are at least approximately 200 mg $kg^{-1}$ of dry weight.

35. The process of claim 33, wherein the *Pteris* fern plant is *P. vittata* and arsenic levels in a root portion of the live plant are at least approximately 80 mg $kg^{-1}$ of dry weight.

36. The process of claim 33, wherein the *Pteris* fern plant is *P. Cretica Rowerii* and arsenic levels in a frond portion of the live plant are at least approximately 150 mg $kg^{-1}$ of dry weight.

37. The process of claim 33, wherein the *Pteris* fern plant is *P. Cretica Rowerii* and arsenic levels in a root portion of the live plant are at least approximately 30 mg $kg^{-1}$ of dry weight.

38. The process of claim 33, wherein the *Pteris* fern plant is *P. Cretica Parkerii* and arsenic levels in a frond portion of the live plant are at least approximately 150 mg $kg^{-1}$ of dry weight.

39. The process of claim 33, wherein the *Pteris* fern plant is *P. Cretica Parkerii* and arsenic levels in a root portion of the live plant are at least approximately 30 mg $kg^{-1}$ of dry weight.

40. The process of claim 33, wherein the *Pteris* fern plant is *P. Cretica Albo-lineata* and arsenic levels in a frond portion of the live plant are at least approximately 150 mg kg$^{-1}$ of dry weight.

41. The process of claim 33, wherein the *Pteris* fern plant is *P. Cretica Albo-lineata* and arsenic levels in a root portion of the live plant are at least approximately 50 mg kg$^{-1}$ of dry weight.

42. The process of claim 33, wherein the *Pteris* fern plant is *P. Quadriavrita* and arsenic levels in a frond portion of the live plant are at least approximately 150 mg kg$^{-1}$ of dry weight.

43. The process of claim 33, wherein the *Pteris* fern plant is *P. Quadriavrita* and arsenic levels in a root portion of the live plant are at least approximately 50 mg kg$^{-1}$ of dry weight.

44. A process for removing a pollutant through an excised plant part, comprising:
- excising a live part of a fern plant selected from the group consisting of: *P. vittata, Polystichum polyblepharum, Dryopteris flixmas, Adiantum hispidulum, Didynachlaena trunvatula*, and *Nephrolepis exaltata;*
- applying the excised plant part to an environment site containing arsenic pollutant; and
- removing a portion of the arsenic through contact with the excised plant part.

45. The process of claim 44, wherein the excised plant part includes: an excised leaflet.

46. The process of claim 45, wherein the environment site includes: a contaminated ground water, contaminated surface water, or contaminated wetland.

47. The process of claim 45, wherein the environment sites includes: a contaminated soil.

48. The process of claim 45, wherein the plant part is from *P. vittata.*

49. The process of claim 45, wherein the plant part is from *Polystichum polyblepharum.*

50. The process of claim 45, wherein the plant part is from *Dryopteris flixmas.*

51. The process of claim 45, wherein the plant part is from *Adiantum hispidulum.*

52. The process of claim 45, wherein the plant part is from *Adiantum hispidulum.*

53. The process of claim 45, wherein the plant part is from *Didynachlaena truncatula.*

54. The process of claim 45, wherein the plant part is from *Nephrolepis exaltata.*

* * * * *